United States Patent [19]
Householder

[11] Patent Number: 5,290,292
[45] Date of Patent: Mar. 1, 1994

[54] SUTURELESS HUMAN EYE GLOBE ROTATION INSTRUMENT

[76] Inventor: John A. Householder, 1382 Hanover La., Ventura, Calif. 93001

[21] Appl. No.: 866,860

[22] Filed: May 29, 1992

[51] Int. Cl.$^5$ .............................................. A61B 17/00
[52] U.S. Cl. .................................... 606/107; 606/1; 128/20
[58] Field of Search ................ 128/20; 606/1, 107, 606/138, 161, 162; 24/67.9, 546, 579; D28/35-38

[56] References Cited

U.S. PATENT DOCUMENTS

| | | | |
|---|---|---|---|
| D. 119,329 | 3/1940 | Leyne | D28/36 |
| 1,168,574 | 1/1916 | Spurr | 128/20 |
| 3,198,244 | 8/1965 | Mairson | 24/546 |
| 3,490,455 | 1/1970 | Illig | 606/107 |
| 3,957,035 | 5/1976 | Chassaing | 606/107 |
| 4,037,589 | 7/1977 | McReynolds | 606/107 |
| 4,321,916 | 3/1982 | McKee | 128/20 |
| 5,022,124 | 6/1991 | Yiin | 24/67.9 |
| 5,070,860 | 12/1991 | Grounauer | 128/20 |
| 5,171,254 | 12/1992 | Sher | 128/20 |
| 5,174,279 | 12/1992 | Cobo et al. | 606/107 |

Primary Examiner—Peter A. Aschenbrenner
Assistant Examiner—Glenn K. Dawson
Attorney, Agent, or Firm—Mark D. Miller

[57] ABSTRACT

An instrument for use in human cataract or glaucoma eye surgery which is inserted into the inferior cul-de-sac of the eye in order to rotate the eyeball downward for exposure of the upper eyeball sclera for surgery. The present instrument avoids the need for sutures or stitches to rotate the eyeball down, thereby avoiding the possibility of ptosis, and unnecessary wounds and their associated possibilities of hemorrhage, discomfort, slow healing and infection. The instrument includes a pair of arms with intermediate curls and a terminating crossbar.

6 Claims, 2 Drawing Sheets

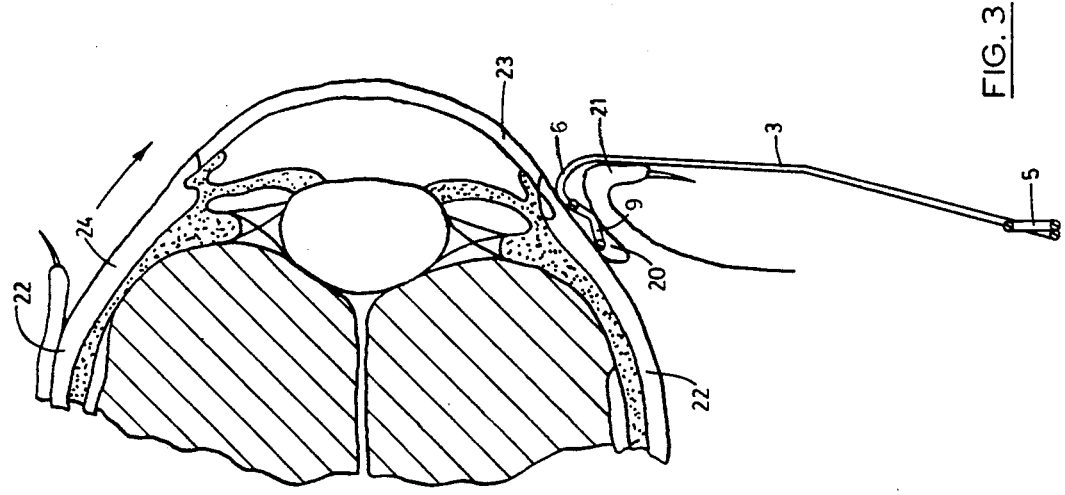
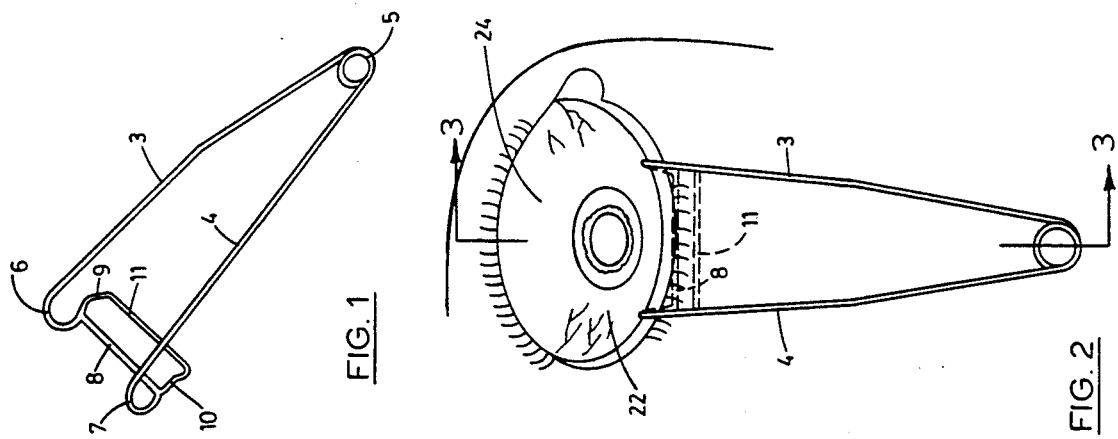

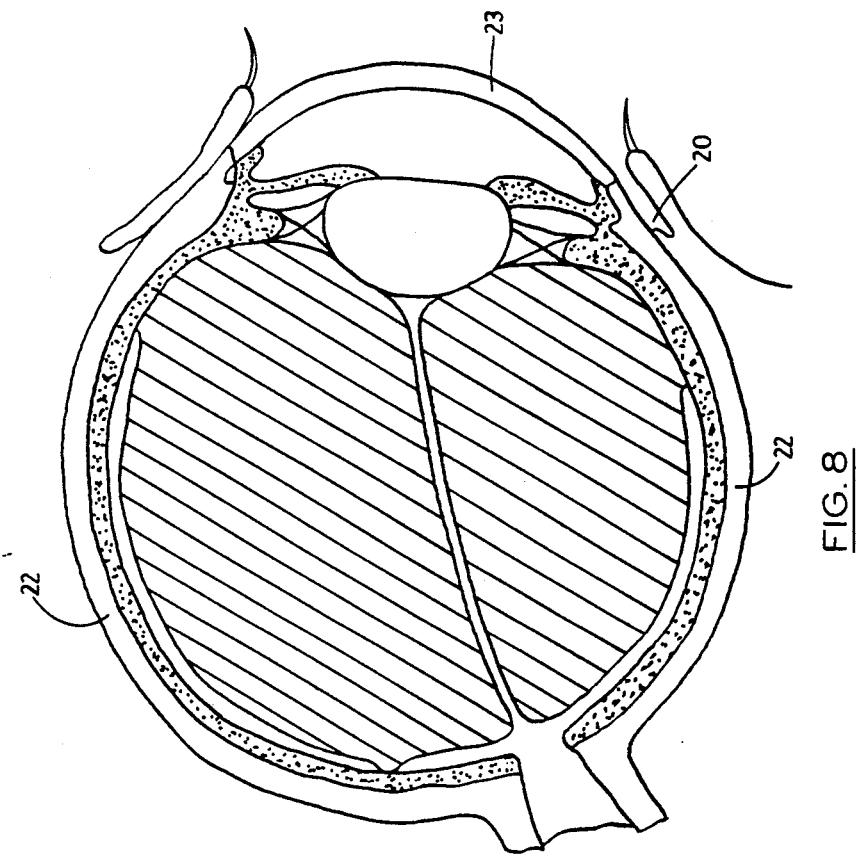
FIG. 8
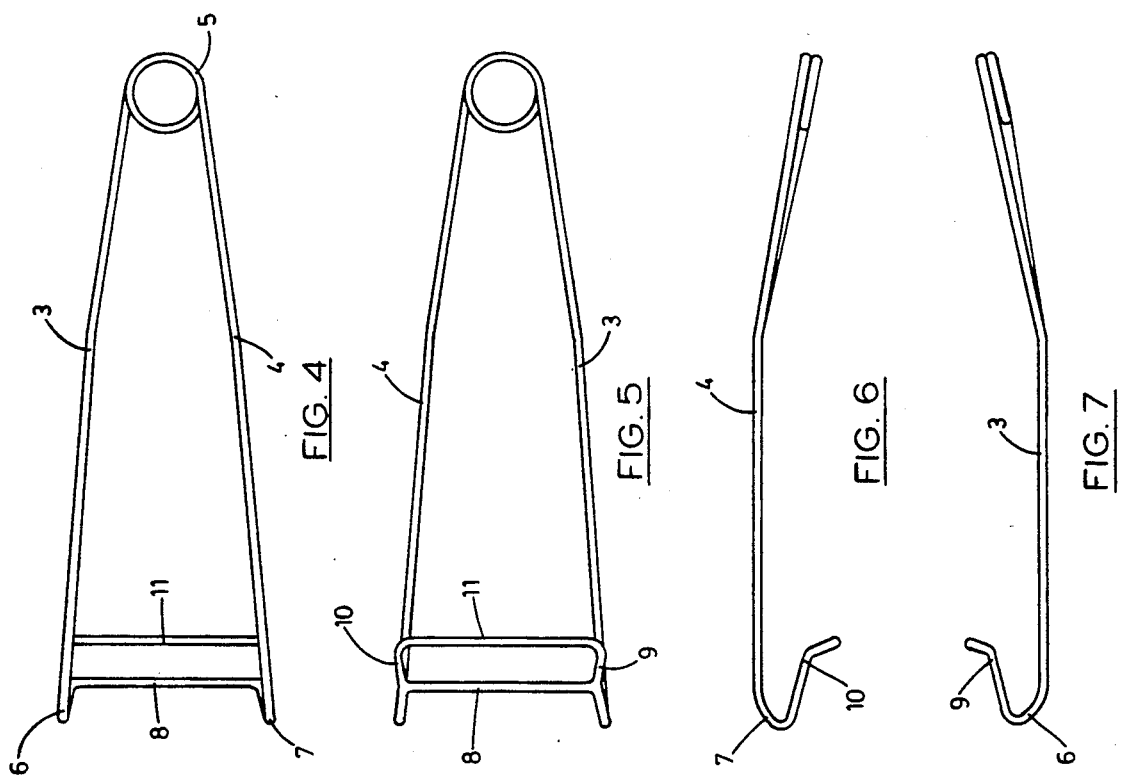
FIG. 4
FIG. 5
FIG. 6
FIG. 7

SUTURELESS HUMAN EYE GLOBE ROTATION INSTRUMENT

BACKGROUND OF THE INVENTION

The present invention relates to medical instruments utilized in human eye surgery. In particular, the invention relates to a speculum that is specially designed for use in cataract and glaucoma eye surgery to rotate the human eye globe down without a suture.

SUMMARY OF THE INVENTION

In the practice of medicine concerning the human eye, there are two common medical procedures which involve surgery on the eye: the removal of cataracts, and the treatment of glaucoma. Each of these procedures requires that the surgeon be able to make an opening on the top of the eyeball in the sclera, in order to access the lens inside the eyeball. Thus, it is important that the eyeball be rolled downward at the beginning of such an operation.

It is well known among physicians that when the human eye experiences pain, the eyeball has a tendency to roll up. This is known as Bell's phenomenon. In the rare event that the pain block wears off before the end of surgery, Bell's phenomenon can be triggered by the stimulus associated with eye surgery. This phenomenon is just the opposite of what is needed by the surgeon in cataract or glaucoma surgery.

In order to rotate the eyeball (eye globe) downward, the practice among eye surgeons for approximately the past 40 years has been the use of a suture that pulls the eyeball down so that the upper sclera is exposed for surgery. Specifically, a suture is attached to the muscle tendon of the superior rectus muscle of the eye. This muscle and tendon, among others, control the movement of the eye. By attaching a suture underneath the tendon and then pulling the suture around the upper eye lid, the eye globe can be rotated downward providing the necessary exposure for surgery.

There are several drawbacks to the suture method. The most important of these is the possibility of ptosis, or drooping, of the upper eye lid. The attachment of a suture to the tendon of the superior rectus muscle coupled with the prolonged tension placed on the muscle often results in weakening of the muscle and ptosis. This condition may last for a few weeks or months, and in some cases can be permanent.

Another drawback of the suture method is the wound that results from the suture. The suture wound may be uncomfortable, it takes time to heal, and it exposes the eye to the possibility of disfiguring hemorrhage and the rare possibility of infection. For most cataract surgery, no other sutures or stitches are necessary. The incisions in the eyeball are usually made in such a way that they heal without sutures or stitches. Thus, the elimination of this last single suture from these types of operations can avoid the unnecessary risk of ptosis, dramatically improve the eye healing process, reduce discomfort, and reduce the possibility of disfiguring hemorrhage and infection.

It is therefore a primary object of the present invention to provide a speculum for use in human eye surgery that rotates the eyeball downward without the need for a suture.

It is a further important object of the present invention to provide a speculum for use in human eye surgery that avoids the possibility of ptosis from attaching a suture to the tendon of the superior rectus muscle of the eye.

It is a further important object of the present invention to provide a speculum for use in human eye surgery that avoids the need for creating a wound from a suture.

It is a further object of the present invention to provide a speculum for use in human eye surgery that avoids the possibility of disfiguring hemorrhage associated with a wound created from a suture.

It is a further object of the present invention to provide a speculum for use in human eye surgery that avoids the possibility of infection associated with a wound created from a suture.

It is a further object of the present invention to provide a speculum for use in human eye surgery that avoids the discomfort associated with a wound created from a suture.

It is a further object of the present invention to provide a method for performing cataract eye surgery without the need for a suture.

It is a further object of the present invention to provide a speculum for use in human eye surgery that is of simple design, may be easily manufactured and is of durable construction.

BRIEF DESCRIPTION OF THE DRAWINGS

FIG. 1 is a perspective view of the present invention.

FIG. 2 is an environmental view of the present invention showing it in place below the eye, causing the eye to be rotated downward.

FIG. 3 is a side cutaway view of the present invention showing it in place below the eye along line 3—3 of FIG. 2.

FIG. 4 is a top view of the invention.

FIG. 5 is a bottom view of the invention.

FIG. 6 is a side view of the invention.

FIG. 7 is an opposite side view of the invention.

FIG. 8 is a side cutaway sketch of the major parts of the human eye organ.

DETAILED DESCRIPTION OF THE DRAWINGS

Referring to the drawings wherein like reference characters designate like or corresponding parts throughout the several views, and referring to FIGS. 4 and 6, it is seen that the invention has a modified triangular shape when viewed from the top, and a shape which resembles an inverted snow sled when viewed from the side. Referring particularly to FIG. 1, it is seen that the invention includes a pair of arms 3 and 4 which are joined at one end at junction 5. Each of said arms 3 and 4 may be straight, or may include a bend in the shape of an elbow at approximately the midpoint of each arm. The opposite ends of arms 3 and 4 each has a downward inside curl 6, 7 of between 60 and 90 degrees from horizontal, which curls may be parallel for each arm.

Below curls 6 and 7 is an optional cross bar 8 which connects the arms together, spacing them apart at a distance less than the diameter of a human eye globe. Below the optional cross bar 8 the arms extend slightly at 9 and 10, and are finally connected by cross bar 11. Each of the extensions of the arms at 9 and 10 may be straight, or may have a very slight downward outside curl of between 10 and 45 degrees in order to conform to the shape of the eye globe. Curls 9 and 10 extend in the opposite direction of curls 6 and 7, so that when the invention so equipped is viewed from the side, curl 6 and 9 of arm 3 (and curl 7 and 10 of arm 4) disclose a modified "S" shape.

DESCRIPTION OF THE PREFERRED EMBODIMENTS

In the preferred embodiment, the present invention is made of smooth stainless steel wire or other smooth rigid material. It is designed to be inserted into the inferior cul-de-sac 20 of the eye. The cul-de-sac is attached to the lower eye lid 21 as well as to the eye globe 22 just below the cornea 23. The curled ends of the invention 6,7 are inserted into inferior cul-de-sac by sliding it therein. The outer smooth edges of curls 6 and 7 touch gently against the eye globe 22, and the arm extensions 9 and 10 fit into the cul-de-sac. Extensions 9 and 10 may be curled in order to conform more closely to the curve of the eye globe. Optional cross bar 8 may be placed intermediate arm extensions 9 and 10 to provide stability The invention should be sufficiently sized so that the distance between curls 6 and 7 (sometimes defined by cross bar 8) is wide enough that curls 6 and 7 do not come into direct contact with the cornea 23.

In surgery, the eye globe will usually rotate freely once the pain block has been performed so that only gentle tension is enough to rotate the globe downward. After the invention is inserted into the inferior cul-de-sac, tension is applied to the opposite end 5 of the invention in the direction of the patient's feet by means of a sterile rubber band or the like.

The insertion of the invention into the cul-de-sac and the application of tension to its opposite end 5 pulls and rotates the eye globe 22 down because of the presence of the invention. This rotation exposes the upper sclera 24 surface of the eyeball for surgery without the need for a suture.

The preferred embodiment described above is but one of many possible structures of the invention which may accomplish the same objective. For example, curves 9 and 10 may be straightened or exaggerated depending on the size and shape of the patient's eye. The angle of curves 6 and 7 may be likewise widely varied according to particular patient circumstances and conditions. The length of cross bar 8 may be varied according to the size of the eye globe, and if extra bracing is not required cross bar 8 may be eliminated entirely. Thus, the invention may be of different sizes, lengths and widths for different shaped eyeballs and different surgery conditions.

It is to be understood that variations and modifications of the present invention may be made without departing from the scope thereof. It is also to be understood that the present invention is not to be limited by the specific embodiments disclosed herein, but only in accordance with the appended claims when read in light of the foregoing specification.

I claim:

1. An instrument for rotating the globe of a human eye downward during eye surgery comprising a pair of arms which are joined at one end forming a joint, and a rubber band attached to said joint, wherein each of said arms includes a first portion which cooperatively extends away from said joint along a horizontal axis, a second portion in which the arms cooperatively curl downward from the horizontal axis forming a first set of curls, and a third portion in which opposite ends of the arms each extend further to a terminating cross bar, said terminating cross bar connecting said opposite ends together transverse to a longitudinal axis of each of the arms, whereby when the instrument is placed in the inferior cul-de-sac and tension is applied to the rubber band the eye globe rotates.

2. The instrument described in claim 1 wherein an inside arc defined by said first set of curls is between 60 and 90 degrees from the horizontal axis.

3. The instrument described in claim 1 wherein a second cross bar parallel to the terminating cross bar is provided connecting the first set of curls of the pair of arms transverse to the longitudinal axis of each of said arms.

4. The instrument described in claim 1 further comprising a second set of curls, said second set of curls being curled in the opposite direction of said first set of curls and being provided in said arms between said first set of curls and said terminating cross bar.

5. The instrument described in claim 4 wherein an outside arm defined by said second set of curls is between 10 and 45 degrees in the opposite direction from said first set of curls.

6. The instrument described in claim 1 wherein each of said arms includes a slight bend approximately midway between the joint and said first set of curls.

* * * * *